(12) United States Patent
Arieli et al.

(10) Patent No.: US 9,198,640 B2
(45) Date of Patent: Dec. 1, 2015

(54) SYSTEM AND METHODS FOR PROVIDING INFORMATION RELATED TO A TISSUE REGION OF A SUBJECT

(75) Inventors: Yoel Arieli, Jerusalem (IL); Israel Boaz Arnon, Neve Tsuf (IL)

(73) Assignee: Real Imaging Ltd., Lod (IL)

( * ) Notice: Subject to any disclaimer, the term of this patent is extended or adjusted under 35 U.S.C. 154(b) by 0 days.

(21) Appl. No.: 13/319,086

(22) PCT Filed: May 5, 2010

(86) PCT No.: PCT/IL2010/000364
§ 371 (c)(1),
(2), (4) Date: Nov. 6, 2011

(87) PCT Pub. No.: WO2010/128508
PCT Pub. Date: Nov. 11, 2010

(65) Prior Publication Data
US 2012/0050321 A1    Mar. 1, 2012

Related U.S. Application Data

(60) Provisional application No. 61/213,093, filed on May 6, 2009.

(51) Int. Cl.
*A61B 8/08* (2006.01)
*A61B 5/00* (2006.01)
*A61B 6/00* (2006.01)
*A61B 5/01* (2006.01)

(52) U.S. Cl.
CPC ............. *A61B 8/5238* (2013.01); *A61B 5/0077* (2013.01); *A61B 6/502* (2013.01); *A61B 6/5247* (2013.01); *A61B 8/0825* (2013.01); *A61B 5/01* (2013.01)

(58) Field of Classification Search
CPC ................ G09G 5/14; G09G 2340/10; G09G 2340/125; G06T 11/60; G06T 15/503
See application file for complete search history.

(56) References Cited

U.S. PATENT DOCUMENTS

| | | | |
|---|---|---|---|
| 2002/0183992 A1* | 12/2002 | Ayache et al. | ..................... 703/2 |
| 2003/0123056 A1 | 7/2003 | Barnes et al. | |
| 2006/0209019 A1* | 9/2006 | Hu | ................................ 345/156 |
| 2007/0110293 A1 | 5/2007 | Arnon | |
| 2007/0238997 A1 | 10/2007 | Camus | |
| 2008/0031409 A1 | 2/2008 | Sarment et al. | |
| 2008/0132781 A1* | 6/2008 | Redel | ............................. 600/419 |
| 2009/0270678 A1* | 10/2009 | Scott et al. | .................... 600/109 |

FOREIGN PATENT DOCUMENTS

WO    WO 2008/042486    4/2008
WO    WO 2010/128508    11/2010

OTHER PUBLICATIONS

International Search Report and the Written Opinion Dated Aug. 17, 2010 From the International Searching Authority Re. Application No. PCT/IL2010/000364.

(Continued)

*Primary Examiner* — Maurice L McDowell, Jr.

(57) ABSTRACT

A system for providing information related to a tissue region of a patient is provided. The system includes a user interface configured for co-displaying medical imaging information of the tissue region and visible light information of the tissue region.

18 Claims, 3 Drawing Sheets
(2 of 3 Drawing Sheet(s) Filed in Color)

(56) References Cited

OTHER PUBLICATIONS

Chiu et al. "Automatic Class-Specific 3D Reconstruction From a Single Image", Computer Science and Artificial Intelligence Laboratory, Technical Report, MIT-CSAIL-TR-2009-008, 11 P., Feb. 18, 2009.

International Preliminary Report on Patentability Dated Nov. 17, 2011 From the International Bureau of WIPO Re. Application No. PCT/IL2010/000364.
Office Action Dated Jul. 3, 2013 From the Israel Patent Office Re. Application No. 216155 and Its Translation Into English.
Office Action Dated Jul. 10, 2014 From the Israel Patent Office Re. Application No. 216155 and Its Translation Into English.

* cited by examiner

SYSTEM AND METHODS FOR PROVIDING INFORMATION RELATED TO A TISSUE REGION OF A SUBJECT

RELATED APPLICATIONS

This application is a National Phase of Patent Application No. PCT/IL2010/000364 having International filing date of May 5, 2010, which claims the benefit of priority of U.S. Provisional Patent Application No. 61/213,093 filed May 6, 2009. The contents of the above applications are all incorporated herein by reference.

FIELD AND BACKGROUND OF THE INVENTION

The present invention relates to a system for providing information related to a tissue region of a subject and in particular to a system and method for co-displaying medical imaging information and visible light information of the tissue region of the subject.

Breast cancer is the second leading cause of cancer death in women after lung cancer, thus prevention and early diagnosis of breast cancer are of foremost importance.

Numerous studies have shown that early detection saves lives and increases treatment options. Since early stage breast cancer does not produce symptoms, the American Cancer Society recommends a screening mammogram and a clinical breast examination every year for women over the age of 40.

X-ray mammography is currently the most widely used screening modality for breast cancer.

Although mammography is routinely used for breast cancer detection, this approach has limited detection capabilities especially in cases of dense-breasted women, such as those having high content of fibroglandular tissues. Because fibroglandular tissues have higher x-ray absorption than the surrounding fatty tissues, portions of breasts with high fibroglandular tissue content are not well penetrated by x-rays and thus the resulting mammograms contain little or no useful diagnostic information.

To traverse these limitations, mammography is oftentimes supplemented by ultrasound examinations as well as replaced or supplemented by magnetic resonance imaging.

Although combined imaging data can dramatically increase the accuracy of diagnosis, especially when supplemented by image co-registration, there still useful information to be gained from physical examination of breasts, since many physicians feel that breast morphology provides important diagnostic information.

Such physical examination is not possible in cases where diagnosis is provided offsite, for example by expert technicians that review medical images or by remote diagnostic facilities (telemedicine). In such cases the physician does not physically examine the patient and thus has no information related to breast appearance at his or her disposal.

The present inventors propose that supplementing medical imaging information with morphological information can greatly enhance diagnostic accuracy. As such, the present inventors have devised a system which enables co-display of medical imaging information alongside visible image information of a tissue region of interest.

SUMMARY OF THE INVENTION

According to one aspect of the present invention there is provided a system for providing information related to a tissue region of a patient comprising a user interface configured for co-displaying a first image of the tissue region captured by a medical imaging device and second image of the tissue region captured by a visible light capturing device.

According to further features in preferred embodiments of the invention described below, the tissue region is a breast or part of it.

According to still further features in the described preferred embodiments the medical imaging device is selected from the group consisting of an X-ray device, and/or an MRI device and/or an Ultrasound device.

According to still further features in the described preferred embodiments the medical imaging device is a thermography device.

According to still further features in the described preferred embodiments the first image and/or the second image are 2D and/or 3D images.

According to still further features in the described preferred embodiments the system further comprises the medical imaging device and the visible light capturing device.

According to still further features in the described preferred embodiments the medical imaging device is a hyperspectral capturing device.

According to still further features in the described preferred embodiments the medical imaging device includes at least one infrared camera.

According to still further features in the described preferred embodiments the visible light capturing device includes at least one visible light camera.

According to still further features in the described preferred embodiments the user interface includes controls for manipulating the first and/or the second images.

According to still further features in the described preferred embodiments the first and the second images are co-registered.

According to still further features in the described preferred embodiments the first image and/or the second image includes information derived from a series of images captured from different angles with respect to the tissue region.

According to still further features in the described preferred embodiments the first image and/or the second image includes any additional information derived from said medical imaging device.

According to still further features in the described preferred embodiments the first image and/or the second image includes any additional information derived from processed image obtained from said medical imaging device.

According to still further features in the described preferred embodiments the first image and/or the second image includes any additional information derived from processed image obtained from a visible light capturing device.

According to still further features in the described preferred embodiments the first image and/or the second image includes any additional information derived from database.

According to still further features in the described preferred embodiments a simulation of an invasive medical action such as biopsy can be performed and displayed on both images simultaneously.

According to still further features in the described preferred embodiments a simulation of any deformation can be performed and displayed on both images simultaneously.

According to another aspect of the present invention there is provided a method of providing information of a tissue region of a subject comprising co-displaying a first image of the tissue region captured by a medical image device and a second image of the tissue region captured by a visible light capturing device.

According to still further features in the described preferred embodiments the first image and/or the second image includes information derived from a series of images captured from different angles with respect to the tissue region.

According to still further features in the described preferred embodiments the tissue region is a breast.

According to yet another aspect of the present invention there is provided a system for providing information related to a tissue region of a patient comprising a user interface configured for co-displaying medical imaging information of the tissue region and visible light information of the tissue region.

According to still further features in the described preferred embodiments, the system can also display additional information derived from the medical imaging device, the visible light capturing device or their respective processed images.

According to still further features in the described preferred embodiments, the system can simulate an invasive medical procedure such as biopsy and display it on the medical and/or visible light image.

According to still further features in the described preferred embodiments, the system can simulate deformation of the tissue region and display it on the medical and/or visible light image.

The present invention successfully addresses the shortcomings of the presently known configurations by providing a system which co-displays diagnostic imaging information alongside visible information of a tissue region of interest.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic illustration of one embodiment of the present system.

FIG. 2 illustrates the user interface of the present system co-displaying visible light and medical imaging information as viewed from the front of a body.

FIG. 3 illustrates the user interface of the present system co-displaying visible light and medical imaging information as viewed from the side of a body.

DESCRIPTION OF THE PREFERRED EMBODIMENTS

Figure 1:
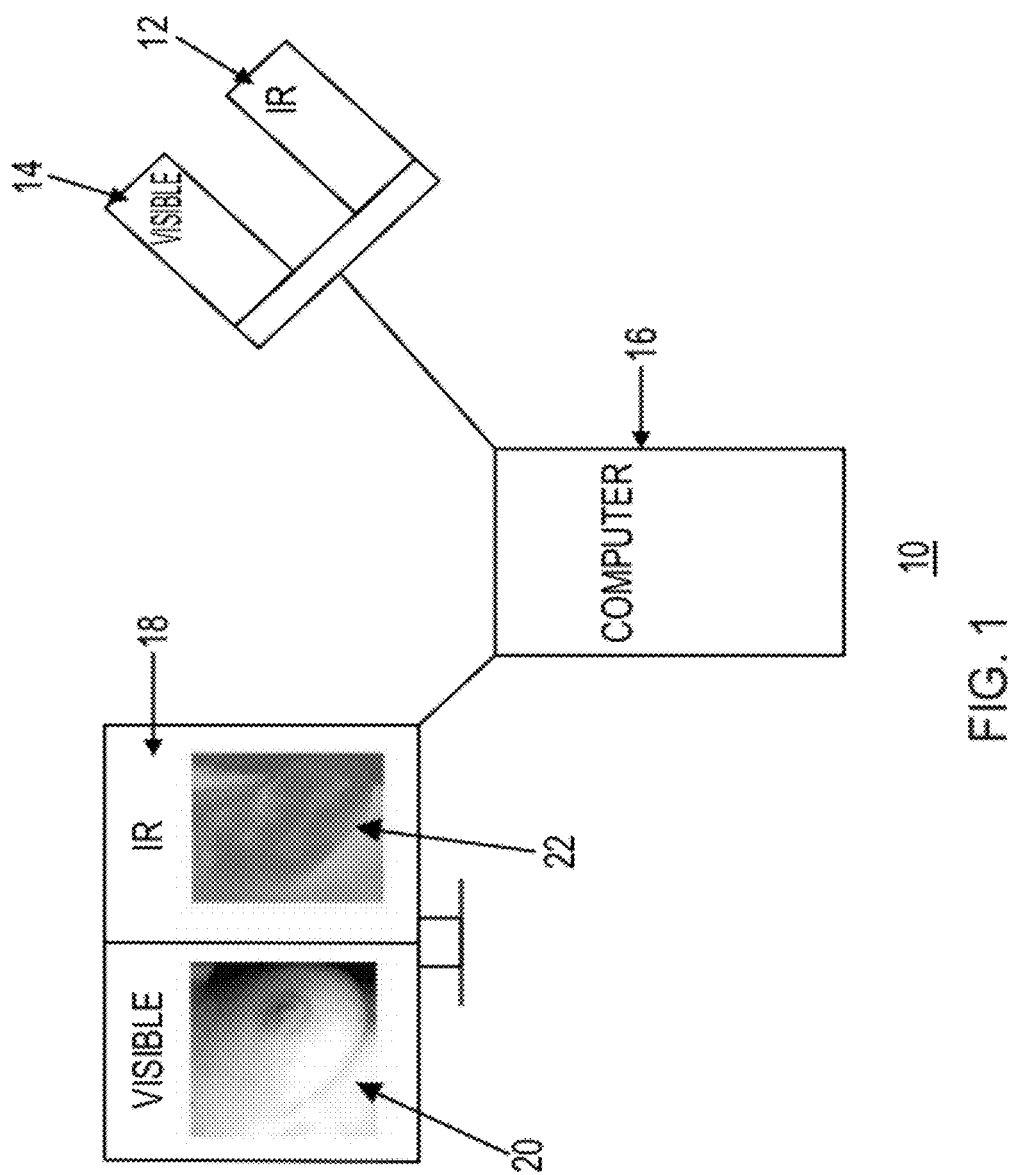

The present invention is of a system and method which can be used to diagnose pathologies and monitor physiological processes such as blood flow in the body. Specifically, the present invention is of a system which supplements medical imaging information with co-displayed visible light information and as such provides a user with valuable diagnostic information, especially in cases where access to the patient is limited such as the case with telemedicine diagnosis.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Systems capable of co-displaying imaging results from two or more medical imaging modalities are known in the art as are systems that enable co-registration of such images. Although combined modality systems can enhance diagnostic accuracy, the present inventors propose that diagnostic accuracy of a medical imaging modality can also be enhanced by visible light information such as that captured by a CCD camera.

Changes in the shape or color of skin can be indicative of an underlying pathology. For example, in the case of joint infection, skin overlying the joint can be discolored or distended. In the case of skin disorders changes in skin color or topography can be indicative of underlying disorders such as cancer.

In such cases and others, information captured by a human eye or an image capturing device such as a CCD or CMOS camera can be useful in diagnosis of pathologies.

As such, the present inventors propose that co-display of such visible light information along with medical imaging information can greatly enhance diagnostic accuracy.

Thus, according to one aspect of the present invention there is provided a system for providing information related to a tissue region of a subject.

The system includes a user interface which is configured for co-displaying medical imaging information alongside or on top of (overlay) visible light information of the tissue region.

As used herein the phrase "medical imaging information" refers to any information provided by a medical imaging modality. Such information can be provided in the form of an image or images or in the form of raw data.

As used herein, the phrase "visible light information" relates to any information pertaining to the shape, surface contour, surface coloration and the like of the tissue region of interest. For example, in the case of breast tissue, visible light information can be used to determine the overall shape of the breast, the surface contour thereof (including surface imperfections, e.g., bumps, pits etc) and the color of the skin overlying the breast.

As used herein, the phrase "tissue region" refers to any tissue region of a body of a subject (e.g. human). Exemplary tissue regions include breasts, joints, appendages, external and internal organs, skin regions and the like.

Thus, the user interface of the present system includes medical imaging information and visible light information. Such a user interface is preferably displayed by a display device which can be an LCD screen, a plasma screen, a projector and the like.

As is mentioned hereinabove, such information can be displayed in the form of raw data or preferably as a medical image. Examples of medical imaging information that can be displayed by the present system include X-ray images, MRI images, Ultrasound images, thermal images and the like.

In any case, the user interface of the present system includes visible light information and medical imaging information. Although the visible light and medical imaging information can be obtained using different fields of view (FOV), they are preferably captured (in terms of angles and field size) or are processed so as to produce identical FOVs or fields of interest.

The visible light and medical imaging information can include 2D data which is captured using a single device positioned at a fixed angle with respect to the tissue region, or preferably the information can include 3D data which is captured by one or more devices positioned at different angles with respect to the tissue region (stereoscopic imaging).

The visible light information can be captured by a stills (digital or film) or an analog or digital video camera. Three dimensional information can be provided by one or more images captured from one or more angles (with respect to the tissue region). Extraction of 3D data from such images can be effected using well known algorithms; the extracted data can then be used to construct a 3D visible model as is further described herein.

For example, in the case of breast tissue 2D imaging can be used to obtain 3D information of the breast which can then be processed and displayed as a 3D object (e.g. rotatable) on a display. Approaches for generating 3D information from 2 or more 2D images are well known in the art of photography and imaging (see for example, www.cs.unc.edu/~mardpubs/PollefeysCACM02.pdf). In addition, applications for generating such images are commercially available, see for example, StereoMaker™ for Windows™. Alternative approaches which utilize a single 2D image for generating 3D objects can also be utilized by the present invention. One such approach is described in "Automatic Class-Specific 3D Reconstruction from a Single Image" by Chiu et al. (Computer Science and Artificial Intelligence Laboratory Technical Report MIT-CSAIL-TR-2009-008 Feb. 18, 2009).

Medical imaging data can be captured using an X-ray device, an MRI device, an ultrasound transducer and the like. In cases where the medical device does not inherently provide 3D data (e.g. simple X-ray and ultrasound devices), information captured from several different imaging planes (by moving the patient or device) can be integrated to provide 3D information using well known approaches.

Systems that can capture the medical imaging and light imaging information from the same FOV (and preferably at the same time), such as the thermal imaging configuration of the present system (further described hereinunder and in U.S. patent application Ser. No. 11/649,290 which is fully incorporated herein), can capture video images which can provide information on the movement of the tissue region imaged and thus provide a measurement of elasticity and the like.

Captured (and processed) information from the medical imaging device and the visible light capturing device are fed into the present system and displayed to a user.

In the most simple configuration of the present system, the visible light image is simply displayed alongside of the medical imaging information and serves to provide information such as contour, surface texture and coloring, overall shape and the like. More advanced configurations can include user interface controls and added functionality which can be used to co-register and co-manipulate the images as well as illustrate movement of the tissue.

Since the visible light and medical imaging information can include 3D data of the same tissue region of interest, co-registration of such images can provide important diagnostic information. In addition, an ability to manipulate the images (e.g. enhance, magnify, zoom, rotate etc) can be used to facilitate diagnosis.

For example, rotation of the medical or light image can be used to view specific areas of the tissue region, this is especially relevant in cases where the tissue region has a volume, such as the case with breasts.

Co-registration of the visible light image and medical image can be used to enable co-manipulation. For example, zooming in on one image results in automatic zoom-in on the other image, tagging a tissue area of interest on a medical image automatically displays the overlying area on the visible light image (see for example FIGS. 2-3), rotating one image results in identical rotation of the other image. The co-registered images can also be superimposed/overlaid in order to provide additional information.

Co-registration also enables to outline or mark a tissue region of interest on a medical image. For example, many medical images include imaging information from the region of interest as well as surrounding regions. Identifying the region of interest in medical images is oftentimes a difficult task to perform. The prior art is replete with methods for automatically identifying and cropping or masking tissue regions of interest in medical images. By co-displaying a co-registered light image of the tissue region of interest, the present system enables a user to mark a tissue area/volume of interest on the visible light image and obtain the same area/volume on the medical image (and vise versa).

Co-registration also enables to display additional information derived from some other medical device or database in both images in the same dimensions and perspective simultaneously.

Co-registration also enables simulation of an invasive medical action such as biopsy on both images simultaneously.

Co-registration also enables simulation of any deformation on both images simultaneously.

To enable the above described functionality, the present system preferably includes a computing platform (e.g. a personal digital assistant, a portable computer, personal computer, a work station or a mainframe), which includes, or is connected to, a display and is capable of receiving and storing the image information as digital data.

The user interface includes interface elements such as tool palettes, buttons, a cursor and the like which enable a user to mark and manipulate the images in the manner described above.

The present system can be directly connected to the medical imaging device and visible light imaging device (see FIG. 1), through for example, physical (e.g. serial or USB cables) or wireless (e.g. WiFi or Bluetooth) communications means. In such cases the imaging information is directly communicated to the computing platform and is processed therein to provide, for example, 3D data, co-registration and the like.

Alternatively, the present system can be remote from the imaging devices (offsite), in which case the preprocessed or processed images can be relayed to the system via a communication network based on satellite, computer and/or cellular communications.

The latter configuration is particularly advantageous in cases where the diagnostic technician/physician has no access to the subject (e.g. telemedicine).

As is mentioned herein, the present system can be utilized to provide information from any tissue of interest. On preferred use of the present system is in diagnosing breast pathologies.

Changes in the shape or color of the breast can be indicative of breast cancer. Some women with breast cancer may initially notice an obvious swelling or deformity of the breast. Some astute women will notice early dimpling of the skin over a superficial lump. This latter symptom is due to involvement of the breast's suspensory ligaments (Ligaments of Astley Cooper) by an underlying tumor. Tumor induced fibrosis can lead to shortening of the ligaments which are indirectly attached to the skin and as a result to skin dimpling. Occasionally large tumors or superficial tumors invade the skin. The skin is fixed to the tumor and may appear slightly blue or violet. Eventually tumor tissue can grow through the skin presenting as a nodule which may eventually ulcerate. Additional information regarding visual manifestation related to breast pathology can be found in "Common Breast Lesions: A Photographic Guide to Diagnosis and Treatment" (Samuel Pilnik, Susan Jormack, Evan Morton Published by Cambridge University Press, 2003 ISBN 0521823579, 9780521823579). Further information regarding breast exams can be found in www.surgerystv.unimelb.edu.au/mah/branatindex.htm.

Referring now to the Figures, one embodiment of the present system (referred to herein as system 10), is shown in FIG. 1.

In this embodiment, system 10 includes medical imaging device(s) 12 (e.g. one or more thermal cameras or IR capturing devices) and co-aligned visible imaging device(s) 14 (e.g. one or more CCD cameras). Devices 12 and 14 are connected to a computing platform 16 which is in turn connected to a display 18.

The image information obtained by devices 12 and 14 is communicated to computing platform 16 and processed thereby to yield two images, a visible light image 20 and a medical image 22 which are displayed side by side on display 18.

Figure 2:
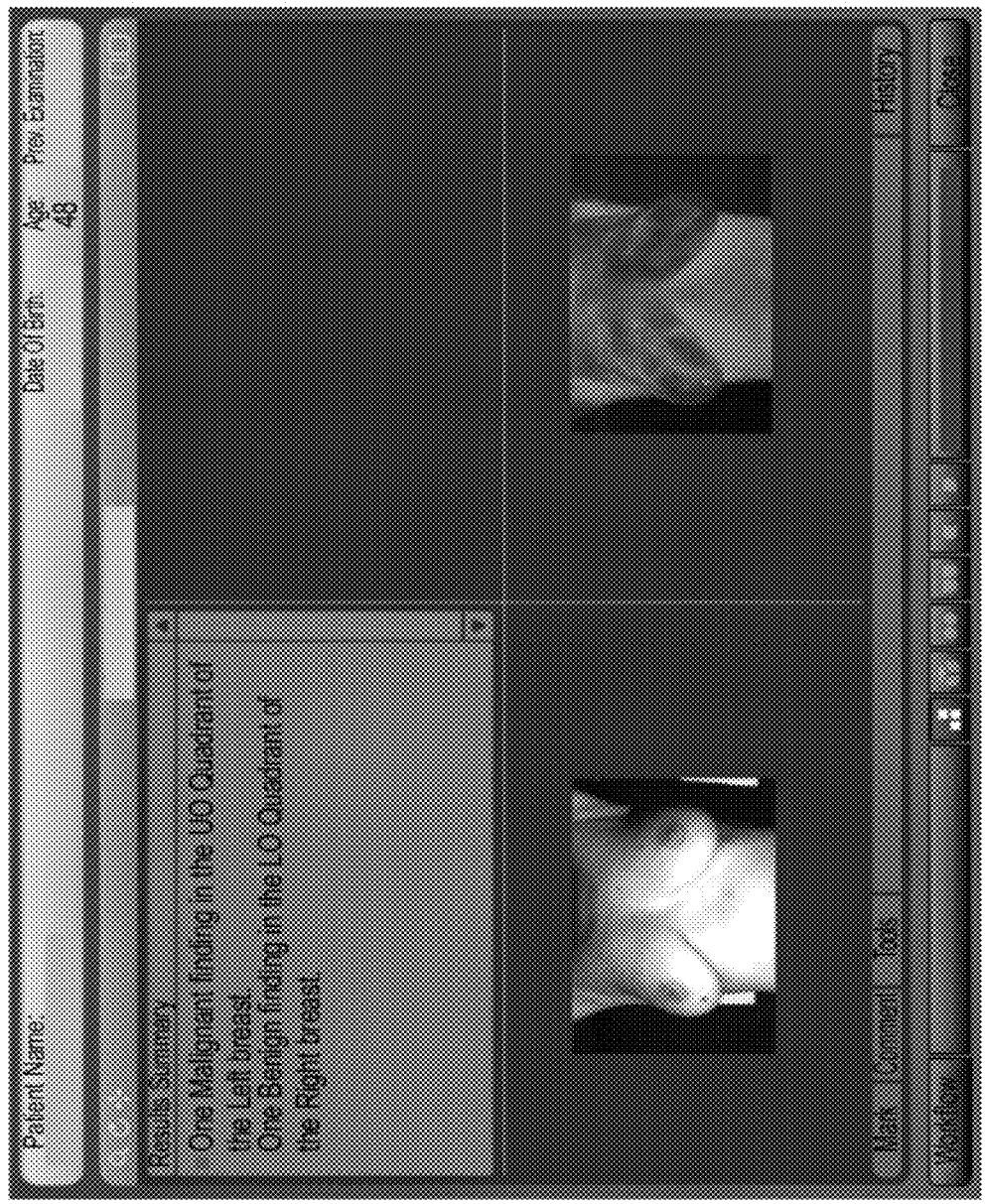
Figure 3:

FIGS. 2-3 illustrate the display of such images from front and side view angles. It will be appreciated that although the information can be obtained by capturing images from such angles, such information can also be obtained by converting the obtained 2D data into 3D image information. In such cases, the resulting image can be rotated through any view angle by the user.

Although image 20 in this case is a real image of the breast (which includes contour and volume information), system 10 can also utilize software which converts the light image data into a model of the tissue.

The reconstruction of a 3D model can be obtained through triangulation using a distinct point on the surface of the object (e.g. in the case of a breast, one can use the nipple) a camera and optionally a projector. Through geometric calculations, one can obtain the angles and distance between the cameras and optionally the projector and use this information to obtain a series of 3D marker points. One approach for triangulation involves use of a projector for projecting a Gray code (a binary code) which consists of stripes on the object. The camera and projector are placed side by side such that the projected stripes are vertical and the triangulation is implemented horizontally (see, U.S. Pat. No. 7,146,036). The principle of this technique is sequentially projecting multiple light patterns onto an object and capturing the reflected patterns with a camera whose position relative to the projector is known (by calibration). Pattern coding allows a set of pattern points (pixels) to be uniquely identified. The decoding process consists of locating the encoded points in the image, provided by the camera when the pattern is being projected on the object. U.S. patent application Ser. No. 11/649,290 which is fully incorporated herein provides further description of such an approach.

The above described approach can be used to construct a 3D model of the breast tissue including any imperfections present in the actual breast. To provide surface coloring, the breast image can then be overlaid on top of the model.

The use of a 3D model is advantageous in that it enables manipulation of the breast tissue (on the display) which mimics a physical exam (e.g. morphological deformation). By using finite element analysis, one can transform such morphological deformation to the medical image, such that it tracks along with the visible light model.

It is expected that during the life of this patent many relevant medical imaging modalities will be developed and the scope of the term medical imaging is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for providing information related to a tissue region of a patient comprising a user interface, a computing platform and a display, wherein said computing platform is configured for co-displaying on said display a first image of the tissue region captured by a medical imaging device and 3D image of the tissue region captured by a visible light capturing device, for simulating over said 3D image a physical examination resulting in morphological deformation of said tissue region, for transforming said morphological deformation to said first image, and for simultaneously displaying said simulation on both said images.

2. The system of claim 1, wherein said tissue region is a breast.

3. The system of claim 1, wherein said medical imaging device is selected from the group consisting of an X-ray device, an MRI device, a hyperspectral device and an Ultrasound device.

4. The system of claim 1, wherein said medical imaging device is a thermography device.

5. The system of claim 1, wherein said first image is a stereoscopic images.

6. The system of claim 1, further comprising said medical imaging device and said visible light capturing device.

7. The system of claim 6, wherein said medical imaging device includes at least one infrared capture device.

8. The system of claim 6, wherein said visible light capturing device includes at least one visible light camera.

9. The system of claim 1, wherein said first and said 3D images are co-registered.

10. The system of claim 9, wherein said first image and/or said 3D image includes information derived from a series of images captured from different angles with respect to the tissue region.

11. The system of claim 1, wherein said computing platform is configured for simulating an invasive medical procedure and simultaneously displaying said simulation on said images.

12. The system of claim 1, wherein said user interface comprises controls for outline or mark a tissue region of interest on said first image.

13. The system of claim 1, wherein said user interface comprises controls for co-manipulating said first and 3D images on said display.

14. The system of claim 1, wherein said first image is a three-dimensional images.

15. A method of providing information of a tissue region of a subject comprising co-displaying a first image of the tissue region captured by a medical image device and a 3D image of the tissue region captured by a visible light capturing device, simulating over said 3D image a physical examination resulting in morphological deformation of said tissue region, transforming said morphological deformation to said first image and simultaneously displaying said simulation on both said images.

16. The method of claim 15, wherein said first image and/or said 3D image includes information derived from a series of images captured from different angles with respect to the tissue region.

17. The method of claim 15, wherein said tissue region is a breast.

18. The method of claim 15, wherein said first image is a three-dimensional images.

* * * * *